United States Patent
Vogeler

(10) Patent No.: US 7,717,860 B2
(45) Date of Patent: May 18, 2010

(54) ELLIPTICAL BIOPSY GUIDE

(76) Inventor: Douglas M. Vogeler, 3587 Little Cottonwood La., Sandy, UT (US) 84092

( * ) Notice: Subject to any disclaimer, the term of this patent is extended or adjusted under 35 U.S.C. 154(b) by 226 days.

(21) Appl. No.: 11/285,321

(22) Filed: Nov. 22, 2005

(65) Prior Publication Data
US 2006/0282011 A1    Dec. 14, 2006

Related U.S. Application Data

(60) Provisional application No. 60/688,476, filed on Jun. 8, 2005.

(51) Int. Cl.
*A61B 10/00* (2006.01)
(52) U.S. Cl. ...................................... 600/564
(58) Field of Classification Search ................ 600/562, 600/564, 565, 567; 606/49
See application file for complete search history.

(56) References Cited

U.S. PATENT DOCUMENTS

| | | | |
|---|---|---|---|
| 164,667 A | 6/1875 | Winslow | |
| 1,515,500 A | 11/1924 | Lee | |
| 1,749,178 A | 3/1930 | Berg | |
| 2,168,766 A | 8/1939 | Dugaw | |
| 2,513,771 A | 7/1950 | Williams | |
| 2,521,161 A | 9/1950 | Grover | |
| 3,502,070 A | 3/1970 | Bliss | |
| 3,774,614 A | 11/1973 | Cook | |
| 3,893,445 A * | 7/1975 | Hofsess | 600/567 |
| 3,990,451 A | 11/1976 | Gibbs | |
| 4,318,358 A * | 3/1982 | Iwamoto | 112/235 |
| 4,431,394 A | 2/1984 | Collett et al. | |
| 4,542,742 A | 9/1985 | Winkelman et al. | |
| 4,576,163 A | 3/1986 | Bliss | |
| 5,123,907 A * | 6/1992 | Romaine | 606/131 |
| 5,507,765 A | 4/1996 | Mott | |
| 5,582,608 A | 12/1996 | Brown | |
| 5,857,995 A | 1/1999 | Thomas et al. | |
| 6,083,003 A | 7/2000 | Kwasnik et al. | |
| D432,874 S * | 10/2000 | Kari | D7/673 |
| 6,371,966 B1 | 4/2002 | Pierce et al. | |
| 6,436,113 B1 | 8/2002 | Burba et al. | |
| 6,626,865 B1 | 9/2003 | Prisell | |
| 6,846,218 B2 * | 1/2005 | Kermode et al. | 450/37 |
| 2004/0030263 A1 * | 2/2004 | Dubrul et al. | 600/565 |

FOREIGN PATENT DOCUMENTS

| | | |
|---|---|---|
| DE | 2811869 | 9/1979 |
| DE | 3642521 | 6/1988 |
| GB | 1555855 | 11/1979 |

* cited by examiner

*Primary Examiner*—Max Hindenburg
*Assistant Examiner*—Fangemonique Smith
(74) *Attorney, Agent, or Firm*—Frost Brown Todd LLC

(57) ABSTRACT

An elliptical biopsy guide comprises a platform and a pair of wings extending from the platform. Each of the wings terminates in a respective curved member. The platform defines a plane, and comprises beveled aperture edges defining an aperture. Each of the aperture edges has a generally elliptical curvature. Each of the wings is angled relative to the plane defined by the platform. A user may exert outward forces with first and second fingers against the insides of respective curved members to hold the elliptical biopsy guide. The elliptical biopsy guide may be positioned over a biopsy site, and a downward force may be applied with the elliptical biopsy guide to provide skin tension or hemostasis. The aperture may be used as a template for excising tissue at the biopsy site.

17 Claims, 2 Drawing Sheets

ELLIPTICAL BIOPSY GUIDE

PRIORITY

This application claims priority from the disclosure of U.S. Provisional Patent Application Ser. No. 60/688,476, entitled "Biopsy Guide," filed Jun. 8, 2005, the disclosure of which is incorporated by reference herein.

BACKGROUND OF THE INVENTION

During biopsies or other procedures, it may be desirable to have an instrument to guide a scalpel, pen, or other implement. While some guiding instruments exist, no one prior to the inventor has created or used the invention described herein.

BRIEF DESCRIPTION OF THE DRAWINGS

It is believed the present invention will be better understood from the following description taken in conjunction with the accompanying drawings, in which like reference numerals identify the same elements. The drawings and detailed description which follow are intended to be merely illustrative and are not intended to limit the scope of the invention.

DETAILED DESCRIPTION OF EMBODIMENTS OF THE INVENTION

The following description should not be used to limit the scope of the present invention. Other examples, features, aspects, embodiments, and advantages of the invention will become apparent to those skilled in the art from the following description, which includes by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive. It should therefore be understood that the inventor contemplates a variety of embodiments that are not explicitly disclosed herein.

Figure 1:
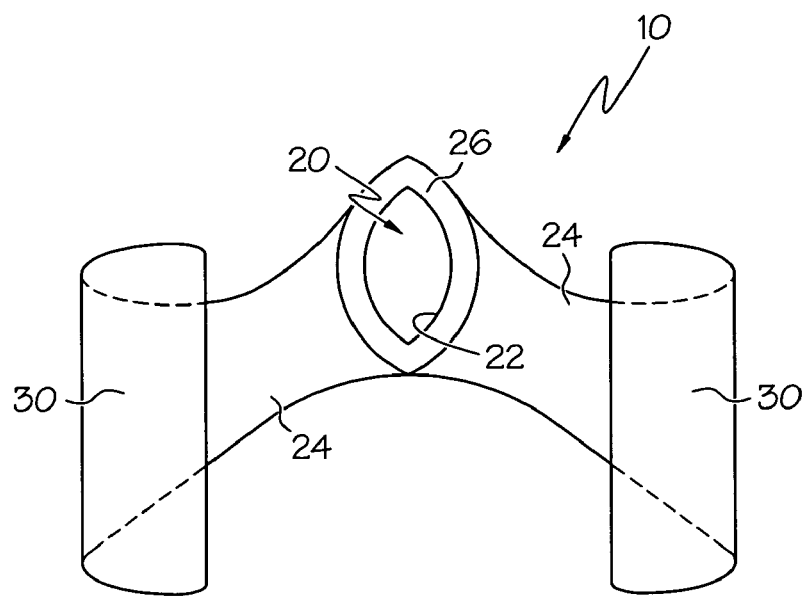
FIG. 1 depicts a top elevational view of an elliptical biopsy guide.
Figure 2:
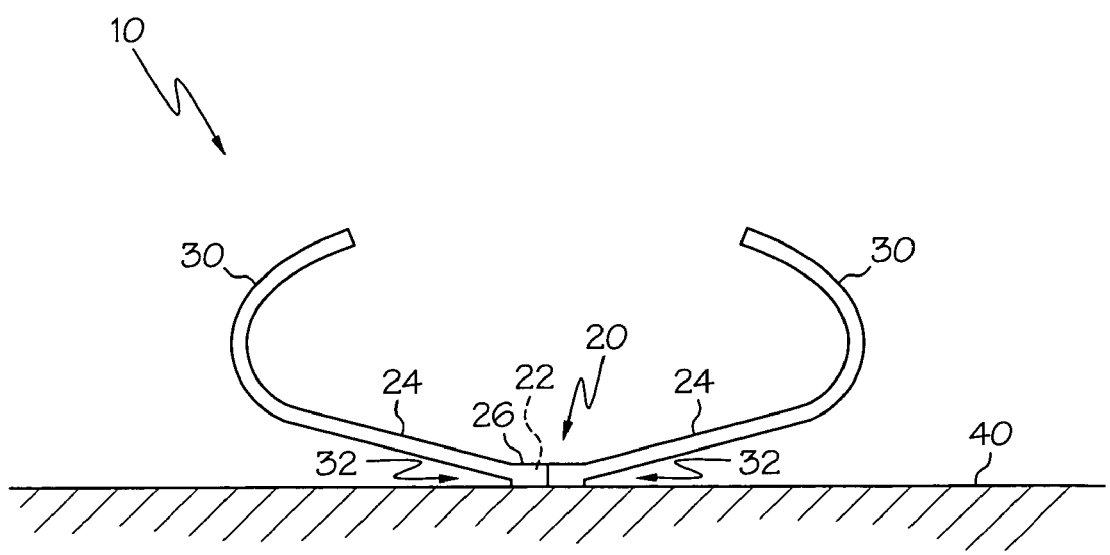
FIG. 2 depicts an end view of the elliptical biopsy guide of FIG. 1, with the elliptical biopsy guide positioned adjacent the skin of a patient.

FIGS. 1 and 2 depict an elliptical biopsy guide (10). The elliptical biopsy guide (10) comprises an aperture (20), wings (24), a platform (26), and a pair of complimentary curved members (30). Platform (26) comprises an aperture edge (22), which defines aperture (20). By surrounding aperture (20), platform (26) thus serves as an aperture rim in this embodiment. Platform (26) of the present example has a width of approximately 3 mm. Of course, any other dimensions may be used. Platform (26) is configured to provide tension and hemostasis when pressed to skin (40). Platform (26) is also configured to provide anchoring points for wings (24) and curved members (30).

As shown, aperture (20) has a substantially elliptical shape. By way of example only, aperture (20) may have a length to width ratio of 2-3 to 1. It will be appreciated, however, that any other ratio may be used, and that aperture (20) may be of any suitable size. It will also be appreciated that aperture (20) need not be elliptical, and may alternatively have any other suitable shape or configuration.

As shown in FIG. 2, elliptical biopsy guide (10) may be positioned adjacent the skin (40) of a patient. Curved members (30) are spaced and dimensioned such that an operator may hold the elliptical biopsy guide (10) naturally stretched between the thumb and index finger away from the lesion or other area of interest. Curved members (30) may thus be used as finger holders. In other words, a respective finger of a user may be positioned adjacent each curved member (30), on the inside of curved members (30), and elliptical biopsy guide (10) may be held by the exertion of outward forces by the user's fingers so positioned. As used herein, the term "finger" shall be understood to include a user's thumb. In addition, to the extent that terms such as "first finger" and "second finger" and the like are used herein, the ordinals in those terms are merely being used to denote separate fingers, and the ordinals in such terms shall not be read to require correspondence with a particular finger. For instance, "first finger" shall not be read as being limited to an index finger or any other particular finger.

Of course, elliptical biopsy guide (10) need not be manipulated by engagement of the operator's fingers with curved members (30). For instance, elliptical biopsy guide (10) may be coupled with another device for holding or otherwise manipulating elliptical biopsy guide (10). In addition, structural variations of curved members (30) may be used as finger holders or as other components for holding or otherwise manipulating elliptical biopsy guide (10).

In the present example, wings (24) are angled upward with respect to aperture (20), such that gaps (32) are present between skin (40) and the portions of wings (24) that are adjacent aperture (20) when elliptical biopsy guide (10) is rested upon skin (40). It will be appreciated that, with such gaps (32), the operator may apply downward pressure against skin (40). Such downward pressure may provide a variety of advantages, including but not limited to hemostasis, skin tension, and/or increasing the ease and/or cleanliness of the cut. Of course, other features or techniques may be used to provide such advantages. It will also be appreciated that wings (24) may be substantially parallel with, perpendicular to, or otherwise oriented relative to aperture (20). In addition, wings (24) may be swept back or forward relative to aperture (20) to assist an operator in keeping his or her hand away from the area being worked on. In another embodiment, one of the wings (24) is oriented or otherwise configured in a manner that is different from the other of the wings (24). Thus, it will be appreciated that wings (24) need not be symmetrical. Still other suitable configurations of aperture (20) and wings (24) will be apparent to those of ordinary skill in the art.

With elliptical biopsy guide (10) positioned and pressure applied, the operator may trace the outline provided by aperture edges (22) with a scalpel, and incise skin (40) in accordance therewith. Where a lesion is the subject of the operation, the same may thus be removed, and skin (40) may thereafter be repaired using any suitable technique.

It will be appreciated that an outline may be traced with a scalpel that is separate from the scalpel used to remove the lesion. Alternatively, a pen or other implement may be used to trace the outline. In yet another embodiment, an act of tracing an outline prior to removing the lesion is not employed. Still other variations of use will be apparent to those of ordinary skill in the art.

During use, elliptical biopsy guide (10) may be used to guide an operator in cutting an incision around a skin lesion greater than 5 mm in diameter with a scalpel. Of course, elliptical biopsy guide (10) may be used to cut incisions around or in lesions of various other sizes. It will also be appreciated that elliptical biopsy guide (10) may be used in a variety of other types of procedures.

In one embodiment, the inside of aperture edge (22) is beveled outward by approximately 10 degrees. Of course, any other angle of bevel may be used. It will be appreciated that such a bevel may be used to guide a scalpel to undermine the skin edge while cutting. It will further be appreciated that such undermining may facilitate better cosmetic closure of the incision and approximation of the skin edges when sutured. Other advantages that may be provided by a beveled aperture edge (22) will be apparent to those of ordinary skill in the art. It will also be appreciated that structural variations of or substitutes for a bevel, including but not limited to an inward bevel, may be used. Alternatively, a bevel may be omitted.

In the present example, elliptical biopsy guide (10) is made of a sterilized disposable plastic material. Alternatively, any other material or combination of materials may be used. By way of example only, wings (24), curved members (30), and/or platform (26) may be formed separately, from the same or different materials, then assembled some time prior to use. For instance, in one embodiment, curved members (30) are formed of plastic, while platform (26) is formed of metal. In another embodiment, the entirety of elliptical biopsy guide (10) is formed of plastic as a homogenous continuum of material. Still other suitable materials and configurations will be apparent to those of ordinary skill in the art.

Figure 3:
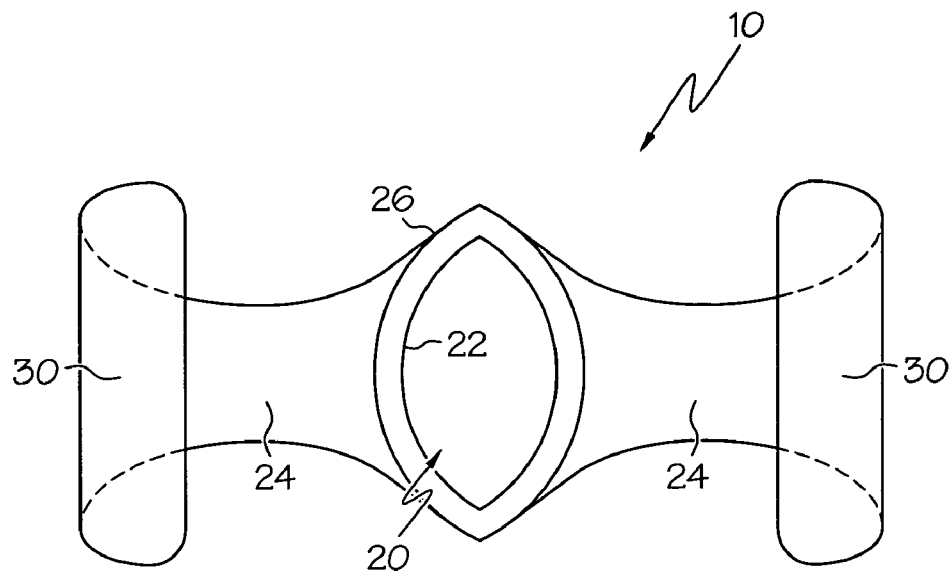
FIG. 3 depicts a top elevational view of an alternative elliptical biopsy guide.
Figure 4:
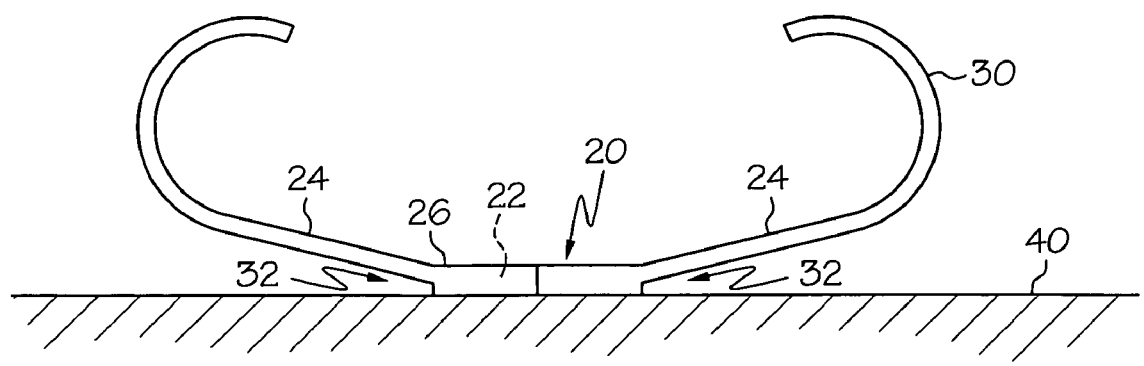
FIG. 4 depicts an end view of the elliptical biopsy guide of FIG. 3, with the elliptical biopsy guide positioned adjacent the skin of a patient.

An alternate embodiment of elliptical biopsy guide (10) is shown in FIGS. 3 and 4. As shown, platform (26), curved members (30), and the configuration of wings (24) relative to aperture (20) are modified in this embodiment. It will be appreciated, however, that these and/or other components of elliptical biopsy guide (10) may be modified in any other suitable way.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings.

What is claimed is:

1. A cutting guide instrument, comprising:
    (a) a platform, wherein the platform defines a plane, wherein the platform comprises:
        (i) at least one aperture edge defining an aperture to provide a biopsy guide, wherein the aperture has a periphery,
        (ii) a first side proximate to the at least one aperture edge,
        (iii) a second side proximate to the at least one aperture edge, wherein the first and second sides are generally opposite relative to the aperture, and
        (iv) a substantially planar blunt portion adjacent to the at least one aperture edge, wherein the substantially planar blunt portion extends about the periphery of the aperture, wherein the substantially planar blunt portion is structurally configured such that the substantially planar blunt portion is positionable directly against a patient's skin without any portion of the cutting guide instrument penetrating the patient's skin;
    (b) a first wing extending from the first side;
    (c) a second wing extending from the second side;
    (d) a first curved member extending from the first wing and generally inwardly relative to the aperture to overlap the first wing, such that an overlapping portion of the first curved member is separated from the first wing to define an empty space between the overlapping portion and the first wing; and
    (e) a second curved member extending from the second wing and generally inwardly relative to the aperture to overlap the second wing, such that an overlapping portion of the second curved member is separated from the second wing to define an empty space between the overlapping portion and the second wing;
    wherein the first curved member curves upwardly then inwardly toward the second curved member, wherein the second curved member curves upwardly then inwardly toward the first curved member;
    wherein the first and second curved members have a size, shape, opposing arrangement, and rigidity such that the first and second curved members are configured to be held by the application of forces exerted outwardly relative to the first and second sides of the platform by respective first and second fingers of a user, with the first and second fingers being positioned under the overlapping portions of the first and second curved members.

2. The cutting guide instrument of claim 1, wherein at least a portion of the at least one aperture edge is generally beveled.

3. The cutting guide instrument of claim 2, wherein the at least a portion of the at least one aperture edge is beveled at approximately 10 degrees.

4. The cutting guide instrument of claim 1, wherein the at least one aperture edge comprises a first aperture edge and a second aperture edge adjacent to the first aperture edge.

5. The cutting guide instrument of claim 4, wherein each of the first aperture edge and the second aperture edge has a generally elliptical curvature.

6. The cutting guide instrument of claim 1, wherein each of the first and second wings is angled relative to the plane defined by the platform.

7. The cutting guide instrument of claim 1, wherein each of the first and second wings extends generally outwardly relative to the aperture.

8. The cutting guide instrument of claim 1, wherein each of the first and second curved members extends generally inwardly relative to the aperture to create a C-shape.

9. The cutting guide instrument of claim 1, wherein the platform has a width of approximately 3 mm.

10. The cutting guide instrument of claim 1, wherein the platform is configured to provide one or both of skin tension and hemostasis upon an exertion of a force downward relative to the plane defined by the platform to skin positioned adjacent to the platform.

11. The cutting guide instrument of claim 1, wherein the aperture has a length to width ratio of approximately 2 through 3 to 1.

12. The cutting guide instrument of claim 1, wherein each of the first and second wings is swept relative to the platform.

13. The cutting guide instrument of claim 1, wherein the combination of the first wing and first curved member is generally symmetrical with the combination of the second wing and the second curved member.

14. The cutting guide instrument of claim 1, wherein each of the first and second wings and the first and second curved members comprises a plastic material.

15. The cutting guide instrument of claim 1, wherein the platform comprises a metal material.

16. The cutting guide instrument of claim 1, wherein the combination of the platform, the first and second wings, and the first and second curved members comprises a homogenous continuum of material.

17. A biopsy guide, comprising:
  (a) a platform, wherein the platform defines a plane, wherein the platform comprises:
    (i) at least one aperture edge defining an aperture to provide a biopsy guide, wherein at least a portion of the at least one aperture edge is generally beveled, wherein at least a portion of the at least one aperture edge has a generally elliptical curvature,
    (ii) a first side proximate to the at least one aperture edge, and
    (iii) a second side proximate to the at least one aperture edge, wherein the first and second sides are generally opposite relative to the aperture;
  (b) a first wing extending from the first side, wherein the first wing terminates into a first curved member inwardly directed in relation to the aperture to overlap the first wing, such that an overlapping portion of the first curved member is separated from the first wing to define an empty space between the overlapping portion and the first wing, and such that a terminal end of the first curved member terminates over a lower portion of the first wing, wherein the first wing is angled relative to the plane defined by the platform;
  (c) a second wing extending from the second side, wherein the second wing terminates into a second curved member inwardly directed in relation to the aperture to overlap the second wing, such that an overlapping portion of the second curved member is separated from the second wing to define an empty space between the overlapping portion and the second wing, and such that a terminal end of the second curved member terminates over a lower portion of the second wing, wherein the second wing is angled relative to the plane defined by the platform; and
  wherein the first curved member curves upwardly then inwardly toward the second curved member, wherein the second curved member curves upwardly then inwardly toward the first curved member;
  wherein the first and second curved members have a size, shape, opposing arrangement, and rigidity such that the first and second curved members are configured to be held by the application of forces exerted outwardly relative to the first and second sides of the platform by respective first and second fingers of a single hand of the user.

\* \* \* \* \*